United States Patent
Li et al.

(10) Patent No.: US 9,157,889 B2
(45) Date of Patent: Oct. 13, 2015

(54) SUBSTANCE SURFACE PROPERTY PARAMETER MEASUREMENT METHOD AND SUBSTANCE SURFACE PROPERTY PARAMETER ANALYSIS SYSTEM THEREOF

(75) Inventors: Hang Li, Bei Bei District (CN); Hualing Zhu, Bei Bei District (CN); Jie Hou, Bei Bei District (CN); Laosheng Wu, Bei Bei District (CN)

(73) Assignee: Southwest University, Bei Bei District, Chongqing (CN)

( * ) Notice: Subject to any disclaimer, the term of this patent is extended or adjusted under 35 U.S.C. 154(b) by 1211 days.

(21) Appl. No.: 13/125,028

(22) PCT Filed: Oct. 13, 2009

(86) PCT No.: PCT/CN2009/074412
§ 371 (c)(1),
(2), (4) Date: Feb. 17, 2012

(87) PCT Pub. No.: WO2010/045846
PCT Pub. Date: Apr. 29, 2010

(65) Prior Publication Data
US 2012/0166097 A1  Jun. 28, 2012

(30) Foreign Application Priority Data

Oct. 20, 2008 (CN) .......................... 2008 1 0232896
Oct. 20, 2008 (CN) .......................... 2008 1 0232897

(51) Int. Cl.
*G01N 21/00* (2006.01)
*G01N 27/60* (2006.01)
*G06F 11/30* (2006.01)

(52) U.S. Cl.
CPC ...................................... *G01N 27/60* (2013.01)

(58) Field of Classification Search
CPC ................................ G01N 27/00; G01N 27/60
USPC ............................................... 702/137, 23–59
See application file for complete search history.

(56) References Cited

U.S. PATENT DOCUMENTS

| 6,915,214 | B2 * | 7/2005 | Dukhin et al. ................... 702/29 |
| 7,075,318 | B1 * | 7/2006 | Zhang et al. ............. 324/754.27 |
| 7,394,279 | B2 | 7/2008 | Lee et al. |

FOREIGN PATENT DOCUMENTS

| CN | 101393238 A | 3/2009 |
| CN | 101393239 A | 3/2009 |

OTHER PUBLICATIONS

Ding, W. et al. "Surface charge properties of neural purplish soil and latosol", Chinese Journal of Soil Science, vol. 38, No. 6, Dec. 2007, pp. 1086-1091. English Abstract included.

*Primary Examiner* — Phuong Huynh
(74) *Attorney, Agent, or Firm* — Merchant & Gould P.C.

(57) ABSTRACT

A method for measuring surface property parameters of a material comprises: performing saturation processing on a surface of a material; mixing the material which has been processed by saturation with an indicating electrolyte solution; after the mixture solution achieves an balance by ion exchange, measuring the balanced concentration values of positive ions of the indicating electrolyte and H+ in the mixture solution; according to the balanced concentration values of positive ions of the indicating electrolyte, calculating surface potential of the material; and according to the surface potential of the material, calculating specific surface area and surface charge density of the material; according to surface charge density of the material, calculating surface electric field intensity; according to surface charge density and specific surface area of the material, calculating total surface charge of the material. A system for measuring surface property parameters of a material can be based on the method.

7 Claims, 1 Drawing Sheet

SUBSTANCE SURFACE PROPERTY PARAMETER MEASUREMENT METHOD AND SUBSTANCE SURFACE PROPERTY PARAMETER ANALYSIS SYSTEM THEREOF

This application is a National Stage Application of PCT/CN2009/074412, filed 13 Oct. 2009, which claims benefit of Serial No. 200810232896.0, filed 20 Oct. 2008 in China and Serial No. 200810232897.5, filed 20 Oct. 2008 in China and which applications are incorporated herein by reference. To the extent appropriate, a claim of priority is made to each of the above disclosed applications.

FIELD OF INVENTION

The present invention relates to colloidal chemistry, interface chemistry, and materials science. In particular, the present invention relates to a method for measuring substance surface property parameters and an analysis system of substance surface property parameters thereof.

BACKGROUND

Surface properties, such as surface potential, surface charge quantity, surface charge density, surface electric field strength and specific surface area of a substance not only are widely used in the scientific research in fields such as colloid and interface science, material science, life science, soil science, ecology and environment science, but also have extensive use in chemical engineering fields such as paper making, cement, ceramics, chemical mechanical polishing (CMP), coal slurry, coating, cosmetics, food industry, mixed dispersion system. Thus, it is important to measure such substance surface property parameters.

In the existing technologies, typically indicator ion adsorption and potential titration are adopted for measurement of substance surface charge quantity. With respect to the indicator ion adsorption, one must first know the percentage of the total adsorption of $H^+$ or $OH^-$ that involve electrostatic adsorption. However, since $H^+$ and $OH^-$ also participate in adsorption of chemical bond, it is impossible to tell the percentage that involves the electrostatic adsorption. Thus, this method cannot measure the surface charge quantity of a system that contains variable charge under any pH values, any electrolyte concentration and any temperatures. The potential titration not only is not suitable for measuring the charge quantity of a system that contains permanent charge, but also its reliability is questionable even for variable charge system. Thus, there is no common measurement method of substance surface charge quantity that suits for various conditions and different systems. Further, no analysis apparatus is available that can conduct such measurement.

In the existing technologies, one method for determining substance surface charge density is based on the following formula:

$$\sigma_0 = \frac{T_C}{S}$$

wherein, $\sigma_0$ is surface charge density, $T_c$ is surface charge quantity, and $S$ is specific surface area.

Since this method requires the parameter of surface charge quantity, the issue faced in measuring the surface charge quantity must exist in determining the surface charge density. In addition, in the above formula of determining surface charge density, a measured data of specific surface area is also required. However, different specific surface area measurement methods may result in wide difference in their measurements. Thus, the reliability of the measurement is hard to control for a surface charge density measurement method that relies on the parameter of specific surface area.

The second method for determining surface charge density is to indirectly obtain a surface charge density value by using relevant formula of Gouy-Chapman upon obtaining a surface potential value of the substance. However, since currently there is no accurate measurement method of surface potential available that can be widely used, there is still difficulties to apply this surface charge density measurement method.

In the existing technologies, the electric field strength is determined based on the following formula:

$$E_0 = \frac{4\pi}{\varepsilon}\sigma_0$$

wherein, $E_0$ is surface electric field strength, $\in$ is medium dielectric constant, in which $\in$ of water is $\in = 8.9 \times 10^{-10}$ $C^2/Jdm$. Due to the dependence to surface charge density, the same issue faced in determining surface charge density also exists in determining surface electric field strength.

In the existing technologies, there are various measurement methods, e.g., normally adopted inert gas adsorption, ion negative adsorption, glycol ethyl adsorption, or glycerine adsorption and the like, to determine substance specific surface area. However, same substance using the various measurement methods results in great difference in the measurement. Even though specific surface area analyzer has been developed based on inert gas adsorption, the analyzer does not suit for measuring specific surface area of expandable substance.

Substance surface potential in the present application refers to potential on the initial surface of diffuse layer or OHP (outer Helmholtz surface). The existing measurement methods for substance surface potential include charge density method, negative adsorption method, positive adsorption method, secondary resonance generation method, pH indicator molecular method, fluorescence generation method, atomic force microscopy, and Zeta potential method, etc. All of the above methods have their own limitations. Charge density method, negative adsorption method, positive adsorption method and secondary resonance generation method are all only suitable for measuring surface potential value of constant charge sample of single electrolyte system under neutral condition. pH indicator molecular method, fluorescence determination method and atomic force microscopy will damage the status of the substance surface per se, and thus the reliability of the measurements is hard to control. Zeta potential method does not measure the surface potential; rather, it measures the potential on the shear surface during electrophoresis. The shear surface is away from the surface defined in the present invention. Zeta potential can be measured under different pHs, electrolytes and temperatures. Thus, in view that currently there is no surface potential measurement method that can be widely used under various conditions and is accurate, Zeta potential is the only choice as a surrogate of surface potential. However, extensive studies in recent years have found that, using Zeta potential method to determine the surface potential only has qualitative meaning. In additional, Zeta potential method has very rigorous requirements to the substance to be measured, i.e., it requires that the particle density of suspension colloid cannot be too high, and the particle size cannot be too large. Even the Zetaprobe-model Zeta potentiometer newly launched by Colloidal Dynamics, LLC (US) can only allow the highest particle density of 60% (volume density). Thus, it is impossible to achieve "original state" measurement for a system having higher density or solid particulate substance.

In view of above, currently there is no reliable and widely applicable method and apparatus that can measure substance surface charge quantity, specific surface area and substance surface potential. Thus, the measurement of substance surface electric field strength and surface charge density that relies on the measurements of substance surface charge quantity and specific surface area respectively also have same defects. Further, there is no method and apparatus in the existing technology that can be used to simultaneously measure the above five (5) parameters from a single experiment.

SUMMARY

In order to solve the above problems, the present invention provides a common measurement method for substance surface property parameters, to enable accurate measurement for surface potential of various types of substances under various conditions, so that simultaneous measurement of substance surface potential, surface charge quantity, surface charge density, surface electric field strength and specific surface area can be achieved.

To realize the objectives of the present invention, a measurement method for substance surface property parameters includes the following steps:

1) performing saturation treatment to a surface of a substance to be measured;

2) mixing the saturated substance to be measured with a solution containing indicator electrolytes; the indicator electrolyte solution includes at least one bivalent metallic positive ion $A^{2+}$ and one monovalent metallic positive ion $B^+$;

3) upon the mixture obtained from step 2) reaching ion-exchange equilibrium, measuring an equilibrium concentration value of the indicator electrolyte positive ion and hydrogen ion in a bulk solution of the mixture;

4) using the concentration value of the indicator electrolyte positive ion obtained from step 3) to the following formula, to obtain a substance surface potential $\phi_0$:

$$\varphi_0 = \frac{RT}{(2\beta_A - \beta_B)F} \ln \frac{c_A^\infty (c_B^0 - c_B^\infty)}{c_B^\infty (c_A^0 - c_A^\infty)}$$

Wherein, $\phi_0$ is substance surface potential, R is gas constant, T is temperature, F is Faraday constant; $c_B^0$ is initial concentration of $B^+$ in solution of the system to be measured which equals to mole number of this added ion divided by total volume of water; $c_A^0$ is initial concentration of $A^{2+}$ in solution of the system to be measured which equals to mole number of this added ion divided by total volume of water. $c_B^\infty$ is the concentration of $B^+$ in the bulk solution when the exchange reaction reaches balance, and $c_A^\infty$ is the initial concentration of $A^{2+}$ in the bulk solution when the exchange reaction reaches balance. $\beta_A$ is a relative effective charge coefficient of $A^{2+}$ that associates with $A^{2+}$ hydrated radius in a system containing "$B^+ + A^{2+}$"; and $\beta_B$ is a relative effective charge coefficient of $B^+$ that associates with $B^+$ hydrated radius in a system containing "$B^+ + A^{2+}$".

Yet, it further includes the following step after step 4):

5) obtaining a specific surface area of the substance based on the surface potential value from step 4);

Yet, it further includes the following step after step 4):

obtaining a surface charge density of the substance based on the surface potential value from step 4);

Yet, it further includes the following step after obtaining the substance surface charge density:

6) obtaining a surface electric field strength based on the surface charge density from step 5).

Yet, it further includes the following step after obtaining the substance surface charge density: obtaining a surface charge quantity of the substance based on the surface charge density and specific surface area from step 5).

Yet, in the step 1), using acid solution to perform saturation treatment to the surface of the substance through constant flow method.

Yet, the acid solution is HCl or $HNO_3$ solution.

Yet, step 1) comprises the following steps:

11) having HCl or $HNO_3$ solution of 0.1 mol/l to flow though the substance to be measured at uniform speed, so that the surface charges of the substance to be measured are all saturated by $H^+$ and $Cl^-$ (or $NO^-_3$);

12) having water to flow though the substance to be measured at uniform speed, to wash off redundant $H^+$ and $Cl^-$ (or $NO^-_3$);

13) drawing interstitial water out of the substance to be measured.

Yet, the negative ion of the indicator electrolyte is same as the acid radical.

Yet, the indicator electrolyte is "$ACl_2$ and $BCl$" or "$A(NO_3)_2$ and $BNO_3$", wherein, $A^{2+}=Ca^2$ or $Mg^{2+}$; $B^+=K^+$ or $Na^+$.

Yet, in step 3), the following steps are used to obtain the equilibrium concentration value of indicator electrolyte positive ion and hydrogen ion in the bulk solution:

31) measuring activity values $a_H$, $a_B$ and $a_A$ of $B^+$, $A^{2+}$ and $H^+$ in the bulk solution.

32) using the activity values from step 31) as initial concentration values, and performing iterative operation through the following steps, to obtain activity coefficients and concentration of $B^+$, $A^{2+}$ and $H^+$.

321) using the activity values from step 31) as initial concentration values of individual ions, and obtaining ionic strength of the system through the following operation:

$$I_i = \frac{1}{2}(2c_i^H + 2c_i^B + 6c_i^A)$$

Wherein, $I_i$ is ionic strength of $i_{th}$ iteration, $c_i^H$ is concentration of $H^+$ of $i_{th}$ iteration, $c_i^B$ is concentration of $B^+$ of $i_{th}$ iteration, and $c_i^A$ is concentration of $A^{2+}$ of $i_{th}$ iteration.

322) Based on the ionic strength, calculating activity coefficients of $B^+$, $A^{2+}$ and $H^+$ through the following formula:

$$\lg \gamma_i^H = \lg \gamma_i^B = -\frac{2618.4 \times T^{-\frac{3}{2}} \sqrt{I_i}}{1 + \sqrt{I_i}}$$

$$\lg \gamma_i^A = -\frac{10473.6 \times T^{-\frac{3}{2}} \sqrt{I_i}}{1 + \sqrt{I_i}}$$

wherein, $\gamma_i^H$, $\gamma_i^B$ and $\gamma_i^A$ are activity coefficients of $H^+$, $B^+$ and $A^{2+}$ of $i_{th}$ iteration, respectively; and T is temperature.

323) Base on the activity coefficients from step 322), calculating equilibrium concentration values of $B^+$, $A^{2+}$ and $H^+$ through the following formula:

$$c_i^H = \frac{a_H}{\gamma_i^H}; \quad c_i^B = \frac{a_B}{\gamma_i^B}; \quad c_i^A = \frac{a_A}{\gamma_i^A}$$

wherein, $c_i^H$, $c_i^B$ 和 $c_i^A$ are equilibrium ion concentration of $H^+$, $B^+$ and $A^{2+}$ of $i_{th}$ iteration, respectively.

Yet, in step 31), using "$H^+$—$B^+$-$A^{2+}$" combined electrode and detector to detect activity of $A^{2+}$, $B^+$ and $H^+$ in the bulk solution.

Yet, in step 32), iterating until (i=k+1)th time, when $(I_{k+1} - I_k)/I_{k+1} < 0.001$, terminating the iteration operation, and using the final result of step 323) as the equilibrium concentration value.

Yet, using the final value I of ionic strength from the iteration operation to calculate effective charge coefficient through the following formula:

$$\begin{cases} \beta_B = 0.0297 \ln I + 1 \\ \beta_A = -0.0297 \ln I + 1 \end{cases}$$

Yet, in step 5), calculating specific surface area of the substance through the following formula, based on the surface potential value from step 4):

$$S = \frac{\kappa V(c_B^0 - c_B^\infty) e^{\frac{\beta_B \varphi_0}{2RT}}}{1.856 c_B^0 - c_B^\infty e^{\frac{\beta_B \varphi_0}{2RT}}}$$

Wherein, V is total volume of water, the unit of which is 1; S is specific surface area, the unit of which is $dm^2/g$; $\kappa$ is Debye-Hückel parameter, the unit of which is $dm^{-1}$, and $\kappa$ is calculated by the following formula:

$$\kappa = \sqrt{\frac{8\pi F^2 (c_H^\infty + c_B^\infty + 3c_A^\infty)}{\varepsilon RT}}$$

Wherein, $\in$ is medium dielectric constant, in which $\in$ of water is $8.9 \times 10^{-10}$ $C^2/Jdm$.

Yet, surface charge density of the substance is calculated through the following formula, based on the surface potential value from step 4):

$$\sigma_0 = \pm \sqrt{\frac{\varepsilon RT}{\pi} \left[ (c_H^\infty + c_B^\infty) \sinh\left(\frac{F\varphi_0}{RT}\right) + \frac{1}{2} c_A^\infty e^{-\frac{2F\varphi_0}{RT}} + c_A^\infty e^{\frac{F\varphi_0}{RT}} - \left(c_H^\infty + c_B^\infty + \frac{3}{2} c_A^\infty\right) \right]}$$

Wherein, $\sigma_0$ is surface charge density, the unit of which is $C/dm^2$.

Yet, in step 6), surface electric field strength of the substance is calculated through the following formula, based on the surface charge density from step 5):

$$E_0 = \frac{4\pi}{\varepsilon} \sigma_0$$

Wherein, $E_0$ is substance surface electric field strength, the unit of which is V/dm.

Yet, surface charge quantity is calculated through the following formula, based on the surface charge density and specific surface area from step 5):

$$T_c = S \times \sigma_0$$

Wherein, $T_c$ is surface charge quantity of the substance, the unit of which is C/g.

The present invention also provides an analysis system for substance surface property parameters based on the measurement method for substance surface property parameters as described above. The analysis system includes a detection system, the detection system comprises:

an ion activity detection unit, for detecting individual ion activity in a solution in a detecting sample container; and a data processing unit, for receiving detecting results from the ion activity detection unit and analyzing surface parameters of a substance to be detected, including:

an ion concentration operation module, for calculating equilibrium ion concentration on the basis of the detecting results received from the ion activity detection unit; and a surface parameter operation module, for receiving the ion concentration calculated from the ion concentration operation module and calculating a surface potential of the substance to be detected based on the ion concentration.

Yet, the surface parameter operation module further calculates specific surface area, surface charge density and surface electric field strength of the substance to be detected based on the surface potential of the substance to be detected, and calculates charge quantity based on the surface charge density and specific surface area.

Yet, the analysis system for substance surface property parameter further comprises a sample treatment unit, comprising:

a sample container, for containing the substance to be measured and liquid; and a liquid intake pipe and a liquid offtake pipe, wherein the liquid offtake pipe is in communication with a bottom of the sample container, the liquid intake pipe is in communication with the sample container; and the liquid offtake pipe is connected to a constant-flow pump.

The sample container further includes a stirring unit.

Yet, the ion activity detection unit includes detecting electrode positioned in the sample container; and a millivoltmeter and an ion activity operator, wherein an input of the millivoltmeter is connected to the detecting electrode, an output of the millivoltmeter is connected to the ion activity operator, the ion activity operator receives potential data detected by the millivoltmeter and converts to ion activity data to output to the ion concentration operation module.

Yet, the activity operator converts potential value detected by the millivoltmeter to individual ion activity value through the following method: upon standardization of individual ions with standard solution of known activity, using Nernst equation to obtain individual ion activity value of the substance to be measured in the activity operator.

Yet, the detecting electrode is "$H^+$-$A^{2+}$-$K^{2+}$—$B^{+}$" combined electrode, in which $A^{2+}$ is a bivalent metallic ion, and $B^+$ is a monovalent metallic ion.

Yet, the detecting electrode is "$H^+$—$K^+$—$Ca^{2+}$" combined electrode, the ion concentration operation module is "$H^+$—$K^+$—$Ca^{2+}$" concentration operation module; the number of millivoltmeters is three (3), inputs of the three millivoltmeters are respectively connected to outputs of $H^+$ electrode, $K^+$ electrode, and $Ca^{2+}$ electrode in the "$H^+$—$K^+$—$Ca^{2+}$" combined electrode, outputs of the three millivoltmeters are respectively connected to inputs of pH operator, $K^+$ activity operator and $Ca^{2+}$ activity operator; upon the pH operator, $K^+$ activity operator and $Ca^{2+}$ activity operator respectively calculating activity of $H^+$, $K^+$ and $Ca^{2+}$, the activity of $H^+$, $K^+$ and $Ca^{2+}$ are outputted to "$H^+$, $K^+$ and $Ca^{2+}$" concentration operation module.

The detection system also includes a temperature probe positioned in the sample container; and an electronic thermometer, an input of which is connected to the temperature probe, and outputs of which are respectively connected to inputs of the pH operator, $K^+$ activity operator, $Ca^{2+}$ activity operator, "$H^+$, $Ca^{2+}$ and $K^+$" concentration operation module and surface parameter operation module.

The simultaneous measurement method for substance surface property parameter and analysis system for substrate surface property parameter of the present invention calculate substance surface potential by measuring the equilibrium ion concentration of the indicator electrolyte, so as to eliminate uncertainty caused by chemical reaction between $H^+$ or non-indicator ion (i.e., any other ion except for $A^{2+}$ and $B^+$) and the substance surface. Under any pH, any electrolyte composition and any electrolyte concentration and temperature, the surface potential of equilibrium system and the concentration of indicator positive ion used always satisfy the following formula:

$$\varphi_0 = \frac{RT}{(2\beta_A - \beta_B)F} \ln \frac{c_A^\infty (c_B^0 - c_B^\infty)}{c_B^\infty (c_A^0 - c_A^\infty)}$$

This ensures that the method and system of the present invention are common measurement method and system applicable for any conditions and any substance types. Accordingly, obtaining substance surface charge density, surface electric field strength, specific surface area and surface charge quantity based on the surface potential measurement suits for any conditions and any substance types. Further, different methods and systems need to be used to conduct measurement for different substance surface property parameters in the existing technology, such parameters can be simultaneously measured by using the method and system of the present invention.

Other advantages, objectives and features of the present invention will be described in the below description to some extent, and to a certain extent will be apparent to people skilled in the art based on the below studies, or can be taught by implementation of the present invention. The objectives and other advantages of the present invention can be achieved and implemented through the description, claims, and drawings that show specific structures.

BRIEF DESCRIPTION OF THE DRAWINGS

To have the objectives, technical solutions and advantages of the present invention more apparent, detailed description will be made in connection with the drawings, wherein.

DETAILED DESCRIPTION OF THE PREFERRED EMBODIMENT

Figure 1:
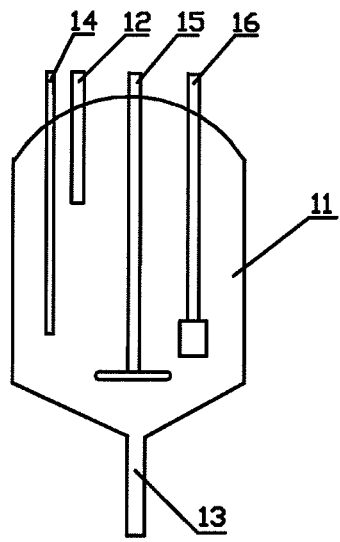
FIG. 1 shows a structure diagram of a sample treatment device of a substance surface property parameter analysis system.

Detailed description of the preferred embodiments of the present invention will be made in connection with the drawings.

The measurement method for substance surface property parameters of this embodiment includes the following steps:

1) Performing a saturation treatment to a surface of an object to be measured, comprising the following steps:

11) Taking 3-5 g sample to be measured into a sample container, and using 150-250 ml HCl solution of 0.1 ml/l to flow though the substance to be measured at a uniform speed of 1 ml/min, to have the surface charges of the object to be measured all saturated by $H^+$ and $Cl^-$; and, using $HNO_3$ solution to perform saturation treatment to the sample to be measured;

12) Using 150-250 ml water to flow though the object to be measured at a uniform speed of 1 ml/min, to wash off redundant $H^+$ and $Cl^-$;

13) Using a constant-flow pump to draw interstitial water out of the object to be measured, until no water flows out.

2) Adding 50 ml mixed solution of KCl, HCl (or KOH) and $CaCl_2$ with known concentration into the sample pool, stirring sufficiently, and then disposing and balancing for over 24 hours; wherein KCl and $CaCl_2$ use as indicator electrolytes, and HCl and KOH use for adjusting pH value. Concentration of the above individual electrolytes can be determined based on the requirements of the researcher, but it is preferred to control the ionic strength of the system during equilibrium within 0.2 mol/l. In this step, other indicator electrolytes can also be used, but there are at least two types of indicator electrolytes, including at least one type of bivalent metallic positive ion, such as $Ca^{2+}$, $Mg^{2+}$, and one type of monovalent metallic positive ion, such as $Li^+$, $Na^+$, $Na^+$. The negative ion of the indicator electrolytes shall be same as the negative ion of the acid in step 11). For example, if using $HNO_3$ solution to perform saturation treatment to the surface of the sample to be measured in step 11), then in this step $NaNO_3$ and $Ca(NO_3)_2$ can be used as indicator electrolytes, and $HNO_3$ and $NaOH$ are used to adjust pH value.

In the following context, description will be made to the present invention by using HCl solution to perform saturation treatment to the surface of the sample to be measured and using KCl and $CaCl_2$ as indicator electrolytes as an example:

3) Upon the mixture from step 2) reaching ion-exchange equilibrium (i.e., balancing for 24 hours under constant stirring; and, balancing for at least 72 hours under non-stirring condition, in which the balancing time may be vary based on the sample type), measuring the equilibrium concentration of the indicator electrolyte positive ion and hydrogen ion in the bulk solution of the mixture, comprising the following steps:

31) Measuring activity values $a_H$, $a_K$ and $a_{Ca}$ of $H^+$, $K^+$, and $Ca^{2+}$ in the bulk solution;

32) using the activity values from step 31) as initial values of corresponding ion concentration, and performing iteration operation through the following steps to obtain activity coefficients and concentration of $K^+$, $Ca^{2+}$ and $H^+$; iterating until to (i=k+1)th time, when $(I_{k+1} - I_k)/I_{k+1} < 0.001$, terminating the iteration operation;

321) using the activity values from step 31) as initial values, and obtaining ionic strength of the system through the following formula:

$$I_i = \frac{1}{2}(2c_i^H + 2c_i^K + 6c_i^{Ca})$$

Wherein, $I_i$ is the ionic strength of $i_{th}$ iteration, the unit of which is mol/l; $c_i^H$ is concentration of $H^+$ at $i_{th}$ iteration, $c_i^K$ is concentration of $K^+$ at $i_{th}$ iteration, and $c_i^{Ca}$ is concentration of $Ca^{2+}$ at $i_{th}$ iteration.

322) Based on the ionic strength, activity coefficients of $Na^+$, $Ca^{2+}$ and $H^+$ can be calculated through the following formula:

$$lg\gamma_i^H = lg\gamma_i^K = -\frac{2618.4 \times T^{-\frac{3}{2}}\sqrt{I_i}}{1+\sqrt{I_i}}$$

$$lg\gamma_i^{Ca} = -\frac{10473.6 \times T^{-\frac{3}{2}}\sqrt{I_i}}{1+\sqrt{I_i}}$$

Wherein, $\gamma_i^H$, $\gamma_i^K$ and $\gamma_i^{Ca}$ respectively are activity coefficients of $H^+$, $K^+$ and $Ca^{2+}$ at $i_{th}$ iteration, and T is temperature, the unit of which is K.

323) Base on the activity coefficients from step 322), the equilibrium concentration values of $K^+$, $Ca^{2+}$ and $H^+$ can be calculated through the following formula:

$$c_i^H = \frac{a_H}{\gamma_i^H};\ c_i^K = \frac{a_K}{\gamma_i^K};\ c_i^{Ca} = \frac{a_{Ca}}{\gamma_i^{Ca}}$$

Wherein, $c_i^H$, $c_i^K$ 和 $c_i^{Ca}$ respectively are the equilibrium ion concentration of $H^+$, $K^+$ and $Ca^{2+}$ at $i_{th}$ iteration;

4) Substituting the equilibrium ion concentration of $K^+$ and $Ca^{2+}$ (equilibrium concentration obtained from last iteration operation) from step 3) into the following formula, to obtain the substance surface potential $\phi_0$:

$$\varphi_0 = \frac{RT}{(2\beta_{Ca} - \beta_K)F}\ln\frac{c_{Ca}^\infty(c_K^0 - c_K^\infty)}{c_K^\infty(c_{Ca}^0 - c_{Ca}^\infty)}$$

wherein, $\phi_0$ is substance surface potential, R is gas constant, T is temperature, F is Faraday constant, $c_K^0$ is concentration of $K^+$ in the system when beginning to add KCl, $c_{Ca}^0$ is concentration of $Ca^{2+}$ in the system when beginning to add $CaCl_2$, $c_K^\infty$ is equilibrium concentration of $K^+$, $c_{Ca}^\infty$ is equilibrium concentration of $Ca^{2+}$, $\beta_K$ is the relative effective charge coefficient of $K^+$ that associates with $K^+$ hydrated radius in the system containing "$K^+$+$Ca^{2+}$"; and $\beta_{Ca}$ is the relative effective charge coefficient of $Ca^{2+}$ that associates with $Ca^{2+}$ hydrated radius in the system containing "$K^+$+$Ca^{2+}$". Using the final value I of ionic strength in the iteration operation to calculate the effective charge coefficient with the following formula:

$$\begin{cases} \beta_K = 0.0297\ln I + 1 \\ \beta_{Ca} = -0.0297\ln I + 1 \end{cases}$$

5) Based on the surface potential value from step 4), specific surface area of the substance is calculated by the following formula:

$$S = \frac{\kappa V(c_K^0 - c_K^\infty)e^{\frac{\beta_K\varphi_0}{2RT}}}{1.856 c_K^0 - c_K^\infty e^{\frac{\beta_K\varphi_0}{2RT}}}$$

Wherein, V is total volume of water, the unit of which is l; S is specific surface area, the unit of which is $dm^2/g$; $\kappa$ is Debye-Hückel parameter, the unit of which is $dm^{-1}$, and $\kappa$ is calculated by the following formula:

$$\kappa = \sqrt{\frac{8\pi F^2(c_H^\infty + c_K^\infty + 3c_{Ca}^\infty)}{\varepsilon RT}}$$

Wherein, $\in$ is medium dielectric constant, in which $\in$ of water is $\in = 8.9 \times 10^{-10}\ C^2/Jdm$.

Based on the surface potential value from step 4), the surface charge density of the substance is calculated by the following formula:

$$\sigma_0 = \pm\sqrt{\frac{\varepsilon RT}{\pi}\left[(c_H^\infty + c_K^\infty)\sinh\left(\frac{F\varphi_0}{RT}\right) + \frac{1}{2}c_{Ca}^\infty e^{-\frac{2F\varphi_0}{RT}} + c_{Ca}^\infty e^{\frac{F\varphi_0}{RT}} - \left(c_H^\infty + c_K^\infty + \frac{3}{2}c_{Ca}^\infty\right)\right]}$$

Wherein, $\sigma_0$ is surface charge density, the symbol of which is same as that of the surface potential and the unit of which is $C/dm^2$;

6) Based on the surface charge density from step 5), the surface electric field strength of the substance is calculated by the following formula:

$$E_0 = \frac{4\pi}{\varepsilon}\sigma_0$$

wherein, $E_0$ is surface electric field strength of the substance, the unit of which is V/dm.

Based on the surface charge density and specific surface area from step 5), the surface charge quantity is calculated by the following formula:

$$T_c = S \times \sigma_0$$

Wherein, $T_c$ is the surface charge quantity of the substance, the unit of which is C/g.

An analysis system of substance surface property parameter of this embodiment comprises a sample treatment device and a detection system. Referring to FIG. 1, the sample treatment device includes a sample container 11 for containing the sample to be measured; and a liquid intake pipe 12 and a liquid offtake pipe 13, wherein the liquid offtake pipe 13 is in communication with a bottom of the sample container 11, the liquid intake pipe 12 is in communication with the sample container 11; and the liquid offtake pipe 13 is connected to a constant-flow pump. A stirring device 15 is provided in the sample container 11.

Figure 2:
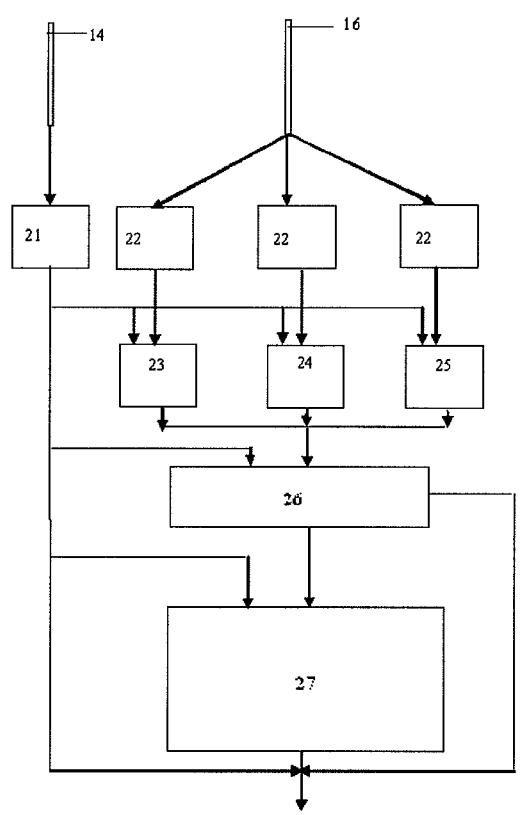
FIG. 2 shows a structure diagram of a detection system of the substance surface property parameter analysis system.

Referring to FIG. 2, the detection system includes:

an ion activity detecting unit for detecting individual ion activity in the solution in the sample container 11, including a detecting electrode 16 disposed in the sample container 11, millivoltmeters 22 and an ion activity operator; the detecting electrode is "$H^+$—$K^+$—$Ca^{2+}$" combined electrode; inputs of three millivoltmeters 22 are respectively connected to outputs of $H^+$ electrode, $K^+$ electrode, and $Ca^{2+}$ electrode of the "$H^+$—$K^+$—$Ca^{2+}$" combined electrode; outputs of the three millivoltmeters 22 are respectively connected to inputs of pH operator 23, $Na^+$ activity operator 24, and $Ca^{2+}$ activity operator 25; the millivoltmeters preferably use high-impedance millivoltmeter; and a data processing unit which can be programmable processor such as single chip microcomputer, the data processing unit receives detected results from the ion activity detecting unit and analyzes the surface parameters of the sample to be measured, comprising:

"H+, Ca2+, and K+" concentration operation module 26 connecting to outputs of the pH operator 23, K+ activity operator 24, and Ca2+ activity operator 25, to receive the detected results from the above operators, to calculate ion concentration, and surface parameter operation module 27 for receiving the ion equilibrium concentration from the "H+, Ca2+, and K+" concentration operation module 26 to calculate surface potential, surface charge quantity, surface charge density, surface electric field strength, and specific surface area of the sample to be measured.

Referring to FIGS. 1 and 2, the analysis system of substance surface property parameter further includes a temperature probe 14 disposed in the sample container 11; and an electronic thermometer 21, input of which is connected to the temperature probe 14, and output of which is connected to inputs of the pH operator 23, K+ activity operator 24 and Ca2+ activity operator 25, concentration operator, and surface property parameter operator.

The pH operator 23, K+ activity operator 24 and Ca2+ activity operator 25 convert the potential values detected by the millivoltmeters into individual ion activity values through the following method: Upon individual ions are standardized by standard solution (the pH value of which shall be same as that of the solution to be measured) with known activity, the activity operator calculates individual ion activity values of the solution to be measured by using Nernst equation.

The "H+, Ca2+, and K+" concentration operation module 26 calculates concentration of K+, Ca2+, and H+ through the following method:

Using the activity values from the pH operator 23, K+ activity operator 24, and Ca2+ activity operator 25 as initial values of individual ion concentration, and performing iteration operation through the following steps:

a) Obtaining the ionic strength of the solution through operation of the following formula:

$$I_i = \frac{1}{2}(2c_i^H + 2c_i^K + 6c_i^{Ca})$$

Wherein, $I_i$ is ionic strength at $i_{th}$ iteration, the unit of which is mol/l; $c_i^H$ is concentration of H+ at $i_{th}$ iteration; $c_i^K$ is concentration of K+ at $i_{th}$ iteration; and $c_i^{Ca}$ is concentration of Ca2+ at $i_{th}$ iteration.

b) Based on the ionic strength, activity coefficients of K+, Ca2+ and H+ at $i_{th}$ iteration can be calculated through the following formula:

$$\lg\gamma_i^H = \lg\gamma_i^K = -\frac{2618.4 \times T^{-\frac{3}{2}}\sqrt{I_i}}{1+\sqrt{I_i}}$$

$$\lg\gamma_i^{Ca} = -\frac{10473.6 \times T^{-\frac{3}{2}}\sqrt{I_i}}{1+\sqrt{I_i}}$$

Wherein, $\gamma_i^H$, $\gamma_i^K$ and $\gamma_i^{Ca}$ respectively are activity coefficients of H+, K+ and Ca2+ at $i_{th}$ iteration; and T is temperature, the unit of which is K.

c) Base on the activity coefficients, concentration values of K+, Ca2+ and H+ for the next iteration operation can be obtained through the following formula:

$$c_i^H = \frac{a_H}{\gamma_i^H};\ c_i^K = \frac{a_K}{\gamma_i^K};\ c_i^{Ca} = \frac{a_{Ca}}{\gamma_i^{Ca}}$$

wherein, $c_i^H$, $c_i^K$ 和 $c_i^{Ca}$ respectively are concentration of H+, K+ and Ca2+ of this iteration. Using such concentration values as the concentration for the next iteration, repeating steps a) to c) to perform iteration operation until the (i=k+1)th time, when $(I_{k+1}-I_k)/I_{k+1}<0.001$, terminating the iteration operation, and using individual ion concentration from last time iteration as the final output equilibrium ion concentration.

The surface parameter operation module 27 receives equilibrium ion concentration (final value of the iteration operation) of K+ and Ca2+ outputted from the "H+, Ca2+, and K+" concentration operation module 26 to substitute to the following formula, to obtain the substance surface potential $\varphi_0$:

$$\varphi_0 = \frac{RT}{(2\beta_{Ca}-\beta_K)F}\ln\frac{c_{Ca}^{\infty}(c_K^0-c_K^{\infty})}{c_K^{\infty}(c_{Ca}^0-c_{Ca}^{\infty})}$$

Wherein, $\varphi_0$ is substance surface potential, R is gas constant, T is temperature, F is Faraday constant. $c_K^0$ is the initial concentration of K+ in the system when beginning to add KCl; and $c_{Ca}^0$ is the initial concentration of Ca2+ in the system when beginning to add CaCl$_2$. The two concentration values are calculated based on the total mole number of individual ions added into the system divided by the total volume of water. $c_K^{\infty}$ is equilibrium concentration of K+; $c_{Ca}^{\infty}$ is equilibrium concentration of Ca2+; $\beta_K$ is the relative effective charge coefficient of K+ that associates with K+ hydrated radius in a system containing "K+ +Ca2+"; and, $\beta_{Ca}$ is the relative effective charge coefficient of Ca2+ that associates with Ca2+ hydrated radius in a system containing "K+ +Ca2+". Using the final value I of ionic strength from iteration operation, the effective charge coefficient is calculated through the following formula:

$$\begin{cases}\beta_K = 0.0297\ln I + 1\\ \beta_{Ca} = -0.0297\ln I + 1\end{cases}$$

The surface parameter operation module 27 calculates the specific surface area of the substance through the following formula based on the substance surface potential $\varphi_0$:

$$S = \frac{\kappa V(c_K^0 - c_K^{\infty})e^{\frac{\beta_K\varphi_0}{2RT}}}{1.856 c_K^0 - c_K^{\infty}e^{\frac{\beta_K\varphi_0}{2RT}}}$$

Wherein, V is the total volume of water, the unit of which is l; S is specific surface area, the unit of which is dm$^2$/g; $\kappa$ is Debye-Hückel parameter, the unit of which is dm$^{-1}$, and $\kappa$ is calculated through the following formula:

$$\kappa = \frac{\sqrt{8\pi F^2(c_H^{\infty}+c_K^{\infty}+3c_{Ca}^{\infty})}}{\varepsilon RT}$$

Wherein, $\in$ is medium dielectric constant, in which $\in$ of water is $\in = 8.9 \times 10^{-10}$ C$^2$/Jdm.

The surface parameter operation module 27 calculates surface charge density of the substance through the following formula based on the surface potential value:

$$\sigma_0 = \pm \sqrt{\frac{\varepsilon RT}{\pi} \left[ (c_H^\infty + c_K^\infty)\sinh\left(\frac{F\varphi_0}{RT}\right) + \frac{1}{2}c_{Ca}^\infty e^{-\frac{2F\varphi_0}{RT}} + c_{Ca}^\infty e^{\frac{F\varphi_0}{RT}} - \left(c_H^\infty + c_K^\infty + \frac{3}{2}c_{Ca}^\infty\right) \right]}$$

Wherein, $\sigma_0$ is surface charge density, the symbol of which is same as that of surface potential and the unit of which is $C/dm^2$.

The surface parameter operation module 27 calculates surface electric field strength of the substance through the following formula based on the surface charge density:

$$E_0 = \frac{4\pi}{\varepsilon}\sigma_0$$

Wherein, $E_0$ is substance surface electric field strength, the unit of which is V/dm.

The surface parameter operation module 27 calculates surface charge quantity through the following formula based on the surface charge density and specific surface area:

$$T_c = S \times \sigma_0$$

Wherein, $T_c$ is surface charge quantity of a substance, the unit of which is C/g.

The above are only preferable embodiments of the present invention, and are not used to limit the present invention. Apparently, people skilled in the art can make various modifications and variations to the present invention without departing from the spirit and scope of the present invention. Therefore, the present invention intends to include all of the modifications and variations that fall into the appended claims or equivalence thereof.

We claim:

1. An analysis system for substance surface property parameter, the analysis system including a detecting system, comprising:

an ion activity detecting unit, for detecting individual ion activity in a solution contained in a sample container adapted to hold a sample having a surface and hold a saturation treatment agent adapted to provide saturation treatment to the sample surface to produce a saturated substance and, the sample container further includes a mixer adapted to mix the saturated substance with a solution containing an indicator electrolyte; wherein the indicator electrolyte solution comprises at least one bivalent metallic positive ion of A2+ and one monovalent metallic positive ion of B+; and data processing unit, for receiving detected results from the ion activity detecting unit and analyzing surface parameters of the substance to be measured, comprising:

ion concentration operation module, adapted to, upon the mixture of the saturated substance with the solution containing the indicator electrolyte reaching ion-exchange equilibrium, measure an equilibrium ion concentration of the indicator electrolyte positive ion and hydrogen ion in a bulk solution of the mixture based on the detected results received from the ion activity detecting unit; and surface parameter operation module, for receiving ion concentration value calculated from the ion concentration operation module and calculating a surface potential of the sample based on the ion concentration value according to the formula $$\varphi_0 = \frac{RT}{(2\beta_A - \beta_B)F} \ln \frac{c_A^\infty(c_B^0 - c_B^\infty)}{c_B^\infty(c_A^0 - c_A^\infty)}$$

wherein, $\phi_0$ is sample surface potential, R is gas constant, T is temperature, F is Faraday constant; $c_B^0$ is an initial concentration of $B^+$ in a system solution to be measured which equals to an mole number of the ion added divided by a total volume of water; $c_A^0$ is an initial concentration of $A^{2+}$ in the system solution to be measured which equals to an mole number of the ion added divided by the total volume of water; $C_B^\infty$ is concentration of $B^+$ in a bulk solution when exchange reaction becomes balanced; $c_A^\infty$ is an initial concentration of $A^{2+}$ in the bulk solution when exchange reaction becomes balanced; $\beta_A$ is an relative effective charge coefficient of $A^{2+}$ that associates with $A^{2+}$ hydrated radius in a system containing "$B^+ + A^{2+}$", and $\beta_B$ is an relative effective charge coefficient of $B^+$ that associates with $B^+$ hydrated radius in a system containing "$B^+ + A^{2+}$".

2. The analysis system for substance surface property parameter according to claim 1, wherein: the surface parameter operation module further calculates a specific surface area, surface charge density and surface electric field strength of the substance to be measured based on the surface potential of the substance to be measured, and calculates a charge quantity based on the surface charge density and specific surface area.

3. The analysis system for substance surface property parameter according to claim 1, wherein: the analysis system for substance surface property parameter further includes a sample treatment unit, comprising:

sample container, for containing the substance to be measured and liquid; and liquid intake pipe and liquid offtake pipe, wherein the liquid offtake pipe is in communication with a bottom of the sample container, the liquid intake pipe is in communication with the sample container; and the liquid offtake pipe is connected to a constant-flow pump;

wherein the sample container further has a stirring device disposed therein.

4. The analysis system for substance surface property parameter according to claim 1, wherein: the ion activity detecting unit includes a detecting electrode disposed in the sample container, millivoltmeters and an ion activity operator, wherein inputs of the millivoltmeters are connected to the detecting electrode, outputs of the millivoltmeters are connected to the ion activity operator; the ion activity operator receives potential data detected by the millivoltmeters to convert into ion activity data and output to the ion concentration operation module.

5. The analysis system for substance surface property parameter according to claim 4, wherein: the activity operator converts the potential data detected by the millivoltmeters into individual ion activity values by the following method: upon standardizing individual ions with standard solution of known activity, using Nernst equation in the activity operator to obtain individual ion activity values of the solution to be measured.

6. The analysis system for substance surface property parameter according to claim 5, wherein: the detecting electrode is "$H^+$-$A^{2+}$-$B^+$" combined electrode, wherein $A^{2+}$ is bivalent metallic ion, and B is monovalent metallic ion.

7. The analysis system for substance surface property parameter according to claim 6, wherein: the detecting electrode is "$H^+$—$K^{2+}$—$Ca^{2+}$" combined electrode, the ion concentration operation module is "$H^+$, $K^+$ and $Ca^{2+}$" concentration operation module; the number of millivoltmeters is three, the inputs of the three millivoltmeters are respectively connected to outputs of $H^+$ electrode, $K^+$ electrode and $Ca^{2+}$ electrode of the "$H^+$—$K^+$—$Ca^{2+}$" combined electrode, the outputs of the three millivoltmeters are respectively connected to inputs of pH operator, $K^+$ activity operator and $Ca^{2+}$ activity operator; upon the pH operator, $K^+$ activity operator and $Ca^{2+}$ activity operator respectively calculating activity of $H^+$, $K^+$ and $Ca^{2+}$, the activity of $H^+$, $K^+$ and $Ca^{2+}$ are output to the "$H^+$, $Ca^{2+}$ and $K^+$" concentration operation module;

the detecting system further includes a temperature probe provided in the sample container; and an electronic thermometer, input of the electronic thermometer is connected to the temperature probe, and output of the electronic thermometer is respectively connected to inputs of the pH operator, $K^+$ activity operator, $Ca^{2+}$ activity operator, "$H^+$, $Ca^{2+}$ and $K^+$" concentration operation module and surface parameter operation module.

\* \* \* \* \*